(12) United States Patent
Penny et al.

(10) Patent No.: US 8,750,984 B2
(45) Date of Patent: Jun. 10, 2014

(54) DEVICE FOR STIMULATION BY MEANS OF ELECTRIC AND MAGNETIC FIELDS, AND FIELD APPLICATORS FOR THIS PURPOSE

(75) Inventors: Stewart Penny, Maroochydore BC (AU); Manfred Krauss, Chemnitz (DE); Roland Fischer, Constance (DE); Werner Schmidt, Chemnitz (DE); Mario Mobius, Leubsdorf (DE)

(73) Assignee: Actegy Ltd., Ascot, Berkshire (GB)

( * ) Notice: Subject to any disclaimer, the term of this patent is extended or adjusted under 35 U.S.C. 154(b) by 1000 days.

(21) Appl. No.: 12/303,389

(22) PCT Filed: Aug. 31, 2006

(86) PCT No.: PCT/EP2006/065839
§ 371 (c)(1),
(2), (4) Date: Dec. 4, 2008

(87) PCT Pub. No.: WO2008/019710
PCT Pub. Date: Feb. 21, 2008

(65) Prior Publication Data
US 2009/0248098 A1   Oct. 1, 2009

Related U.S. Application Data

(63) Continuation of application No. PCT/EP2006/065404, filed on Aug. 17, 2006.

(51) Int. Cl.
*A61N 1/00*   (2006.01)
(52) U.S. Cl.
USPC ............ 607/2; 607/1; 607/3; 607/71; 607/66; 607/67; 607/68; 607/69; 607/70; 607/72; 607/73; 607/74; 607/75; 607/76

(58) Field of Classification Search
USPC .............................................. 607/1–3, 66–76
See application file for complete search history.

(56) References Cited

U.S. PATENT DOCUMENTS

| | | |
|---|---|---|
| 4,889,526 A | 12/1989 | Rauscher et al. |
| 5,156,587 A | 10/1992 | Montone |
| 5,899,922 A | 5/1999 | Loos |
| 6,675,047 B1 | 1/2004 | Konoplev et al. |
| 2005/0080459 A1 | 4/2005 | Jacobson et al. |

FOREIGN PATENT DOCUMENTS

DE    102004024655    1/2005

*Primary Examiner* — Michael Kahelin
*Assistant Examiner* — Mallika D Fairchild
(74) *Attorney, Agent, or Firm* — Volpe and Koenig, P.C.

(57) ABSTRACT

A device for stimulation via electric and magnetic fields is provided. The autonomic/vegetative nervous system can be controlled by signals in the frequency ranges of 0.05 to 0.15 Hz and 0.15 to 0.30 Hz, respectively. By addition of characteristic sinusoidal oscillations between the head and a peripheral area with the corresponding low-frequency sympathetic or parasympathetic control frequency as base oscillation and with application-typical EEG frequencies and higher-frequency sinusoidal oscillations in the range of ca. 250 to 1500 Hz, characteristic stimulation programs are established. These are applied by field applicators in the upper body area and in the lower body. The associated mat applicators distribute field energy. The field applicator is equipped with a combination of a magnetic-field-generating coil arrangement and an electrode arrangement generating the electric field. The electrode generating the electric field can at the same time be designed as a magnetic-field-generating coil.

5 Claims, 17 Drawing Sheets a)

b)

a)

b)

c)

DEVICE FOR STIMULATION BY MEANS OF ELECTRIC AND MAGNETIC FIELDS, AND FIELD APPLICATORS FOR THIS PURPOSE

BACKGROUND

The invention relates to a device for stimulation via electric and magnetic fields, and field applicators for this purpose.

When biological processes are caused or influenced by natural electro-magnetic fields, as shown for example by Koenig [Unsichtbare Umwelt. Der Mensch im Spielfeld elektromagnetischer Kraefte. Eigenverlag Herbert L Koenig, Munich 1986], Marino [Modern Bioelectricity, Marcel Dekker, New York and Basel 1988] and Krauss [QRS-Magnetfeldtherapie—Gegenwart und Zukunft (Plenary address); conference volume "QRS-Magnetfeldtherapie—Gegenwart und Zukunft, 1. Internationales Symposium Quantenmedizin in Forschung und Praxis. Darmstadt/Weiterstadt Apr. 2, 2001; "Die natuerlichen elektromagnetischen Signale in unserer Umwelt und deren Stimulation als QRS®-Magnetfeldtherapie", lecture on the Northern German conference for complementary medicine, Jun. 22-23, 2002 Wilhelmshaven, as well as "Die Mikrostrom-CellVAS®-Therapie" (publication of the company Software+Systeme Erfurt GmbH/Germany 2004)], it is possible to largely reproduce nature using specific fields and in case of an existing deficit hereby stimulate humans and animals. On this note the hypothesis must be assessed, formulated by Itil [Quantitative pharmaco-electroencephalography. Use of computerized cerebral biopotentials in psychotropic drug research. In: Itil, T. M. (Ed.): Modern Problems of Pharmacopsychiatry, Vol. 8: Psychotropic Drugs and the Human EEG. Karger, Basel 1974] as well as Fink [Cerebral electrometry—quantitative EEG applied to human psycho-pharmacology. In: Dolce, G. and H. Kuenkel (Eds): CEAN-computerized EEG-analysis. Fischer, Stuttgart/New York 1975] and proven, among others, via pharmaceutical EEG (Pharmako-EEG) [Herrmann, W. M. and E. Schaerer: Das Pharmako-EEG. Grundlagen, Methodik, Anwendung. Landsberg/Lech/Germany: ecomed 1987 (ISBN 3-609-64170-3)], according to which equivalent EEG-modifications (EEG-electro encephalogram) lead to the same stimulus effects and/or equivalent stimulus effects are connected to the same EEG-modifications.

FIG. 1 shows the previously known primary frequency ranges of physical stimulation.

Fournier [Description des installations dúne station dénregistrement des variations tre's rapides du champ magne'tique terrestre; extrait des Comptes Rendus des séances de l'Acade'mie des Sciences, t. 251, p. 671-673 séance due $1^{er}$ aout 1960] reports on the terrestrial magnetic field measurements performed, in which oscillations were determined with a range of variation of the allocated periods lasting from 30 seconds (=0.03 Hz) to 0.025 seconds (=40 Hz). The upper frequency limit is here equivalent to the EEG and EKG (EKG—electrocardiogram). Koenig [Unsichtbare Umwelt. Der Mensch im Spielfeld elektromagnetischer Kraefte. Eigenverlag Herbert L. Koenig, Munich 1986] has discovered that magnetic fields connected to the activity of the heart have a frequency range from 0.1 to 40 Hz. Accordingly, the upper frequency limits are identical for the earth magnetic field, EKG, and EEG. This may also apply to the lower frequency limit, however no publications in this regard have been found.

The spectrum of amplitudes deduced by Fournier from the measurements of the terrestrial magnetic field showed a resonance point at the Schumann and/or EEG-α-frequency 10 Hz. However, oscillations having periods lasting 4.5 seconds were dominant, which is equivalent to a frequency of 0.22 Hz. This value also coincides with the field of human respiration and/or the parasympathetic nervous system as a component of the autonomic nervous system, as discernible from Schmidt and Thews [Human Physiologie. Second, Completely Revised Edition, Springer Berlin Heidelberg New York 1989]. Accordingly, the mean breathing frequency of adults at rest amounts to 14 breaths/min. (=0.23 Hz), with variations occurring ranging from 9.18/min [=0.15 . . . 0.3 Hz].

Persinger [Possible Cardiac Driving by an External Rotating magnetic Field. Int. J. Biometeor. Vol. 17, No. 3, pp. 263-266, 1973] examined the possibility to control the activity of the heart of rats by an external magnetic field rotating at 0.5 Hz with an intensity of 10-20 Gauss. Here, significantly longer RR-intervals developed than in the control groups (RR-interval . . . amount of time deduced from the peaks of two successive R-waves in the EKG, which is equivalent to the duration of a cardiac period and thus the reciprocal heart frequency). This is the obvious expression for an activation of the parasympathetic nervous system, which as commonly known reduces the heart frequency [Thews, G et R Schmidt: Human Physiologie. Second, Completely Revised Edition, Springer Berlin Heidelberg New York 1989], also in a rat.

Friedmann et al. [Friedmann, H., R. O. Becker and C. H. Bachmann: Effect of Magnetic Fields on Reaction Time Performance. Nature Vol. 213, no. 5079, pp. 949-950, 1967] examined the effectiveness of extremely slow oscillations of magnetic fields on the reaction time of humans. These results were found:

Static fields with a strength of 0.5 mT and/or 1.7 mT cause no statistically proven influence.

A static field in combination with an alternating field showed statistically proven results, though: The test persons treated with a field having a parasympathetic—frequency 0.2 Hz had a longer reaction time in reference to the sympathetic—frequency 0.1 Hz.

The latter results show that the frequency 0.1 Hz, that can change the peripheral micro-circulation, coincides with the known Traube-Hering wave as well as an activation of the sympathetic nervous system, while 0.2 Hz correlates to the respiratory frequency and/or the parasympathetic nervous system.

As known from the human physiology [Thews, G et R Schmidt: Human Physiologie. Second, Completely Revised Edition, Springer Berlin Heidelberg New York 1989], all organs of the body, except for the skeletal muscles, are innervated by the vegetative/autonomic nervous system. In addition to influencing the internal organs humorally, there is a second way for controlling cell functions: The vegetative nervous system via its component sympathetic and parasympathetic nervous system, which can be influenced by signals of the frequency ranges 0.05 . . . 0.15 Hz and/or 0.15 . . . 0.30 Hz [Thews, G et R Schmidt: Human Physiologie. Second, Completely Revised Edition, Springer Berlin Heidelberg New York 1989].

In this way, the vegetative nervous system becomes a "control system" for the peripheral vessels, heart, bronchia, intestines, kidney, genitalia, etc.

SUMMARY

Based on the above-mentioned facts, the object of the invention is therefore to provide a further developed device for stimulation via electric and magnetic fields and field applicators particularly suitable for this purpose, with the device having to ensure that a quasi-control of the vegetative nervous system can occur.

This object of the invention is attained according to the features of claim 1, with the sub-claims at least representing beneficial embodiments and further developments.

According to the invention, instead of a fixed frequency 0.1 and/or 0.23 Hz, the overall sympathetic [0.05 . . . 0.15 Hz] or parasympathetic [0.16 . . . 0.30 Hz] frequency range is used in the form of a stimulation frequency impressed from the outside wobbled or swept successively in an arbitrarily fine graduation. Here, beneficially the steps for these ranges are predetermined 0.05; 0.06; 0.07; 0.08; 0.09; 0.1; 0.11; 0.12; 0.13; 0.14; 0.15 Hz and/or 0.16; 0.17; 0.18; 0.19; 0.20; 0.21; 0.22; 0.23; 0.24; 0.25; 0.26; 0.27; 0.28; 0.29; and 0.30 Hz. Here, a respective stimulation period of 30 seconds is sufficient. The mean values of 0.1 Hz (sympathetic nervous system, blood pressure periods, Traube-Hering oscillations) and/or 0.23 Hz (respiration, parasympathetic nervous system) are impressed upon the autonomic nervous system for a longer period of time, approx. 4 minutes.

As experience teaches, a continuous meteorological collection of blood pressure and/or respiratory periodic occurs as well as a constant comparison to the respective target values 0.1 and/or 0.23 Hz. Similar to technical regulatory measures, by stimulating the nervous system with an alternating field of electric or magnetic energy it is tried for the actual values measured to approximate the optimal target values.

According to the invention, this allows a stimulating control of the human autonomic nervous system using the coupled alternating fields including frequencies and/or frequency ranges of approx. 0.1 and/or 0.23 Hz.

In the area of the spinal cord as an essential component of the central nervous system, there are decisive sections for a potential coupling of the information parameters, primarily for the sympathetic and the parasympathetic nervous system via physical stimulation, which according to the invention can be stimulated via field applicators designed with an appropriate structure.

This is achieved, among other things, in that the field applicator system is designed for the upper body such that a concentration of the magnetic flux is adjusted to the center of the upper body of the proband (area of the central nervous system). Also adjusted to the physiological conditions of humans, the applicator system allocated to the lower body is designed such that the distribution of the field energy occurs to both leg areas, with their centers having a certain distance from each other, and thus two field-strengths maxima develop.

Typical cardiovascular stimulation programs can be produced by combining a positive or negative E-field component with a control frequency of the autonomic nervous system as well as other known stimulation frequencies.

Here, according to the invention, an E-field component shall define an electric field created between the foot and the head area. Unlike magnetic fields, this E-field stimulates potential differences. In order to combine the advantages of the stimulation via electric potentials with the effects of magnetic fields a field applicator according to the invention is provided with a combination of a coil arrangement creating a magnetic field and an electrode arrangement creating the electric field. Here, the electrode creating the electric field can simultaneously be embodied as a coil creating a magnetic field.

This represents a principal difference from conventional stimulation realizations via magnetic fields, because in the latter, in addition to the alternating field, a temporarily unchanged portion (DC-portion) can be generated in the stimulation signal, however creating only a constant magnetic field and no potential difference between the area near the head and the cardiovascular periphery.

While the basic structures of previous stimulus-signals are similar in their principles and for example comprise a meandering function with a rising e-function and/or an inclining, overlapping sinus, thus e.g., allowing frequencies in the EEG-frequency range by an appropriate combination of a basic function and a pulse package, an addition of determined sinusoidal oscillations according to the invention can be used with an appropriately low-frequency sympathetic or parasympathetic control frequency as the basic oscillation.

This control frequency, in addition to the E-field component, is interfered with selected n-frequencies of the EEG-range as well as m-frequencies causing biochemical reactions. For example, according to the invention it has been learned via signal-frequency optimizations performed that an aggregation of erythrocytes occurring in the blood-dark field can be dissolved primarily by frequencies ranging from approx. 250 to 1500 Hz. According to the invention, a Fourier sequence with a base oscillation of approx. 250 Hz as well as harmonic oscillations of approx. 500, 750, 1000, 1250, 1500, . . . Hz have been determined as optimal ratios, when the amplitudes of these harmonic oscillations amount to relative portions of ½, ⅓, ¼, ⅕, ⅙, . . . and an overall signal phase shift is realized of 180°. When this electric component, by which the respective magnetic field shall cause the normalization of the erythrocyte aggregation, is called $i_{IIS}(5)$ [iis . . . ion injection signal], in case of a basic oscillation of 250 Hz it is yielded, for example, (A . . . amplitude of the basic oscillation 250 Hz):

$$I_{IIS}(t) = -A[\sin 2\pi 250 t + 0.5 \sin 2\pi 500 t + 0.33 \sin 2\pi 750 t + 0.25 \sin 2\pi 1000 t + 0.2 \sin 2\pi 1250 t + 0.17 \sin 2\pi 1500 t + \ldots ]$$

The signal created in this manner is interfered with the known frequencies of the EEG—range as well as the appropriate control frequency of the autonomic nervous system. Due to the fact that the erythrocytes, particularly their membrane, represent an oscillation system and the optimal frequency (resonance frequency) amounts to approximately 1 kHz, such a separation of erythrocytes can occur by the resonance effect at the membrane. In case of a (pathologic) erythrocyte aggregation the flow features of the blood change. Furthermore, the resonance frequency of this system is reduced by dampening occurring, as known from the theory of (linear) systems. According to the invention, the potential frequency detuning of blood cells is compensated such that the frequency portions included in the signal can pass a defined band width, thus oscillate slightly around a mean frequency.

The fields provided for the stimulation are generated via a special device for creating the fields. This device exchanges the electric signals created in the signal creation device into the energy forms provided for the stimulation. Here, various devices in the form of simple electric coils are known, integrated in a mat applicator. Here, various electric coils are arranged such that they apply a field predominantly induced by a magnetic field. Due to the fact that the operation of the device occurs at frequencies below 1 MHz, almost no electric fields are generated by the known device. The equilibrium of the electric and the magnetic field known from electromagnetic science only develops at a distance of far more than the wavelengths, which even at a frequency of 1 MHz still amounts to approx. 300 m. In the immediate application range of the device the known devices create therefore almost no electric field components at all.

As stated above, the stimulation is particularly effective in combinations of electric and magnetic fields. According to the invention, the device is designed for creating fields from various individual coils or coils in combinations with electrically conductive grids or surfaces is designed for allowing both the feeding of electric currents as well as voltages.

Particularly by the cooperation of the elements it is possible to cause the combination of fields to become effective.

BRIEF DESCRIPTION OF THE DRAWINGS

The invention is explained in greater detail using exemplary embodiments and figures. Shown here are.

DETAILED DESCRIPTION OF THE PREFERRED EMBODIMENTS

Figure 1:
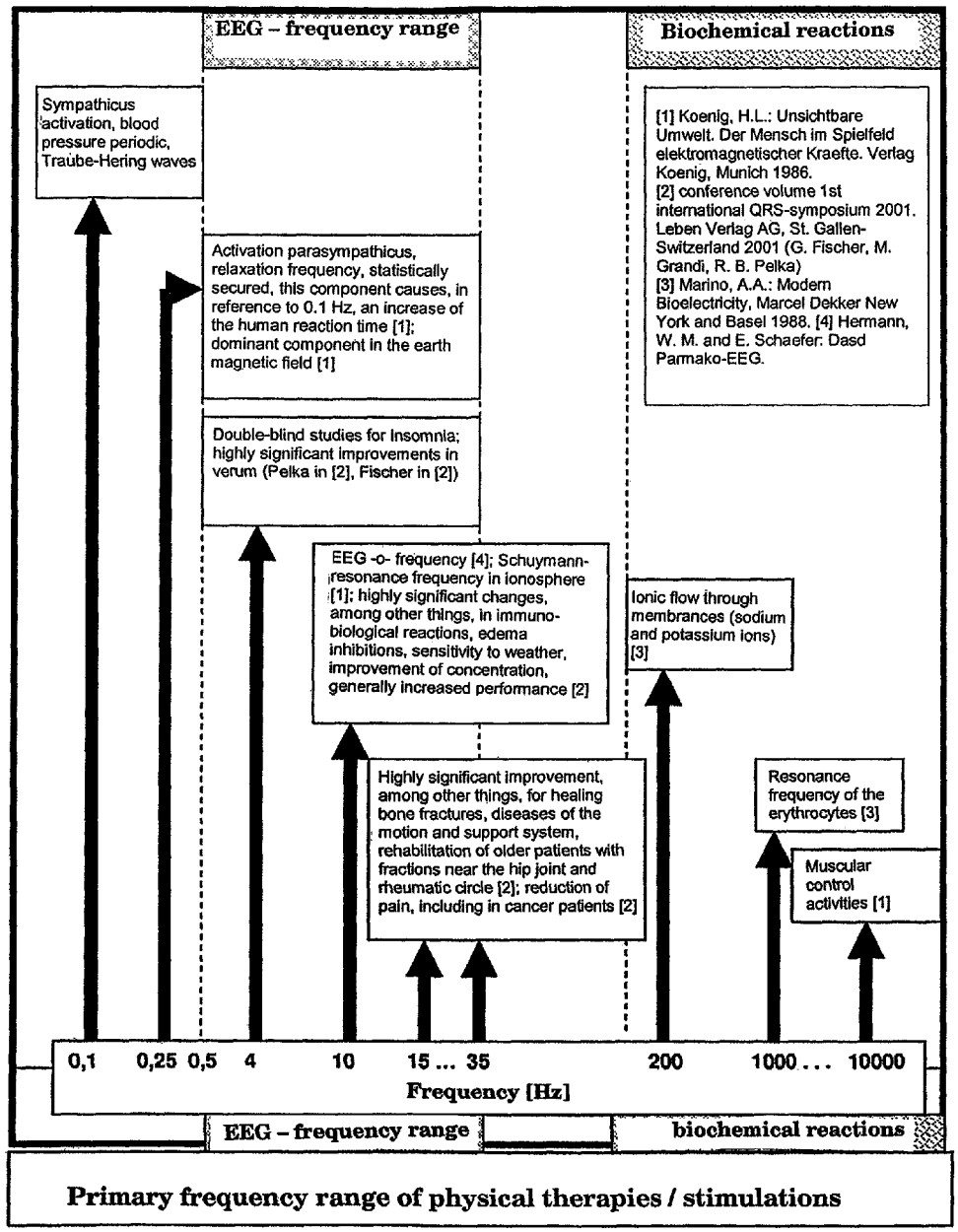
FIG. 1 shows characteristic stimulation frequencies of electric and magnetic fields [from Krauss, M: "Die natuerlichen elektromagnetischen Signale in unserer Umwelt und deren Stimulation aus QRS®-Magnetfeldtherapie." Lecture on the Northern German conference for complementary medicine, 22-23 Jun. 2002, Wilhelmshaven]
Figure 2:
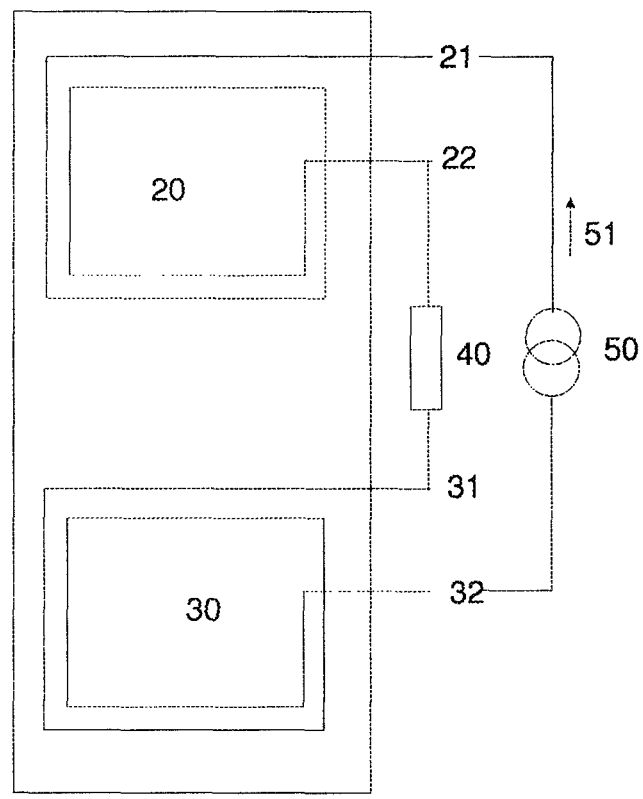
FIG. 2 is a view of a simple device for creating an electric field combined with a magnetic field by transforming electric signals, with the electric field following the magnetic field.

The device according to FIG. 2 is characterized in that the applicator comprises two coil systems 20 and 30, which are spatially arranged such that, on the one hand, a concentration of the effects of the different magnetic fields on the various areas of the effect is achieved and, on the other hand, a potential difference between the coils also leading to the formation of a specific electric field.

The potential difference is created by the voltage dropping via a resistor 40, which is switched between the connector 22 and the connector 31. This circuit achieves that the electric field follows the magnetic field. When the current to create the magnetic field is interfered by direct current (DC-component), additionally the formation of a constant E-field is achieved.

In FIG. 2 two coil systems 20 and 30 are shown with connectors 21 and 22 for the coil system 20 as well as the connectors 31 and 32 for the coil system 30. Using the power source 50, a current 51 is fed to the coil system such that the current first flows through the coil 20, subsequently over the resistor 40 switched between the connectors 22 and 31, is guided into the coil system 30, and subsequently flows back to the power source via the connector 32. The effect of the electric field develops by the voltage drop via the resistor such that an electric potential difference is created between the coil system 20 and 30. The current flow in the coil systems in turn creates the effect of the magnetic field. The current 51 is modulated by the power source 50 in the intensity using the above-described frequencies, so that the electric and magnetic fields can unfold their effect in the manner described.

Figure 3:
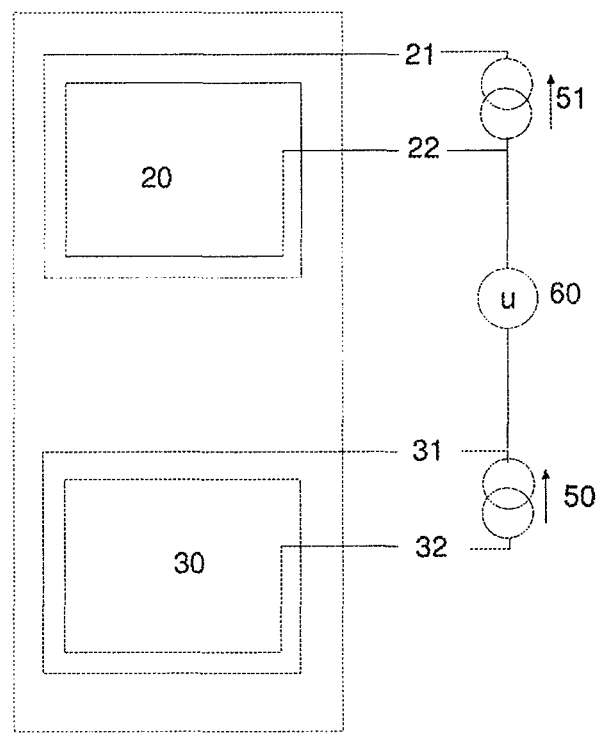
FIG. 3 is an expanded circuit diagram of the device for creating an electric field combined with a magnetic field, with the electric field being controllable independent from the magnetic field.

The arrangement according to FIG. 3 shows an expansion of the functionality of the example according to FIG. 2 by an amended switching.

This allows to separately controlling both the electric field component as well as the magnetic field component. In addition to the improvement of the application of the device, additionally better energy utilization is achieved, because the loss by the Ohm resistance is omitted. Additionally, the direct (current) portion in the control signal for the magnetic field component can be omitted, because this DC-portion can be used in an energy saving manner for the electric field.

FIG. 3 shows in detail: two coil systems 20 and 30 with connectors 21 and 22 for the system 20 and 31 and 32 for the system 30. By the power sources 50 a current, modulated according to the attempted goal, is fed to the coil system, here system 30 is shown. Furthermore, the power source 51 feeds a current into the into the system 20 and creates a second magnetic field in the effective range of this coil system, which can also be controlled by the separate power source, independent from the first coil system with regard to its intensity or composition of frequency. Using a power source 60, an electric potential difference is created between both coil systems, so that an electric field can form between the two coil systems.

Figure 4:
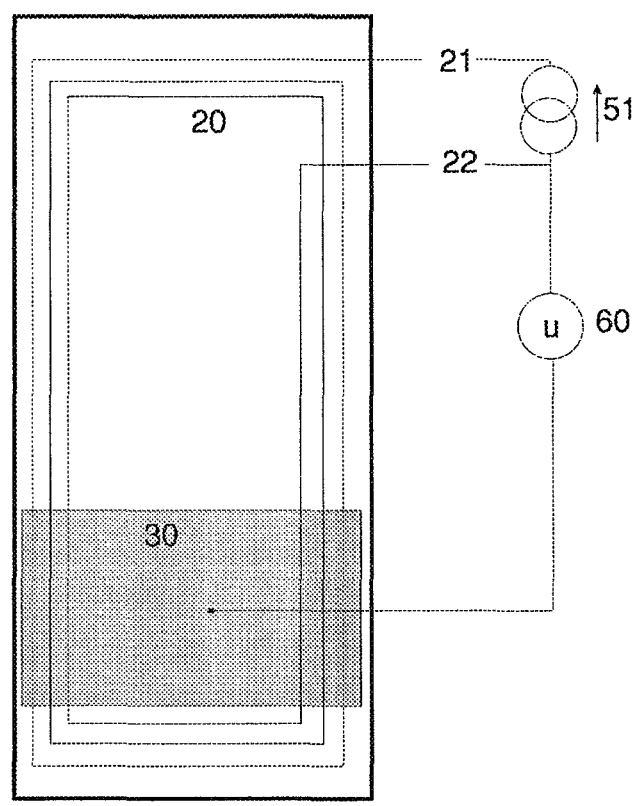
FIG. 4 is a view of an expanded device for creating an electric field combined with a magnetic field.

FIG. 4 discloses an expanded device for creating an electric field combined with a magnetic field, with independent electrode systems being provided for the electric field and the magnetic field, and the magnetic field being created by a single power source and the electric field by a single voltage source.

Two advantages develop from this mat-applicator arrangement. On the one hand, the coil system creating the magnetic field can be designed rather freely and can be oriented optimally for achievement of goals. The electric field can be optimized in the same manner so that both fields can be embodied independent from each other. Another advantage in reference to the arrangements according to FIGS. 2 and 3 is the concentration of the electric field on the side of the applicator that the application originates from. The back thereof shields the electric field such that, on the one hand, no interferences can occur, for example by electric wires below the mat applicator. Additionally, the field embodied appropriately for its application is not disturbed by any other metal surfaces (metal floor, steel reinforcements).

Specifically, FIG. 4 shows a coil system 20 with connectors 21 and 22, which can be constructed in a simple fashion in one plane, for example embedded in a mat. In a second plane, arranged electrically isolated above the plane of the coil system 20, an electrode 30 is arranged, which can be embodied as a closed surface or covering an area in form of individual conductive tapes. The power source 51 controlling the magnetic field feeds the controlling current to the connectors 21 and 22. The voltage source 60 controlling the electric field creates a controlled potential between the electrode 30 and the coil system 20.

Figure 5:
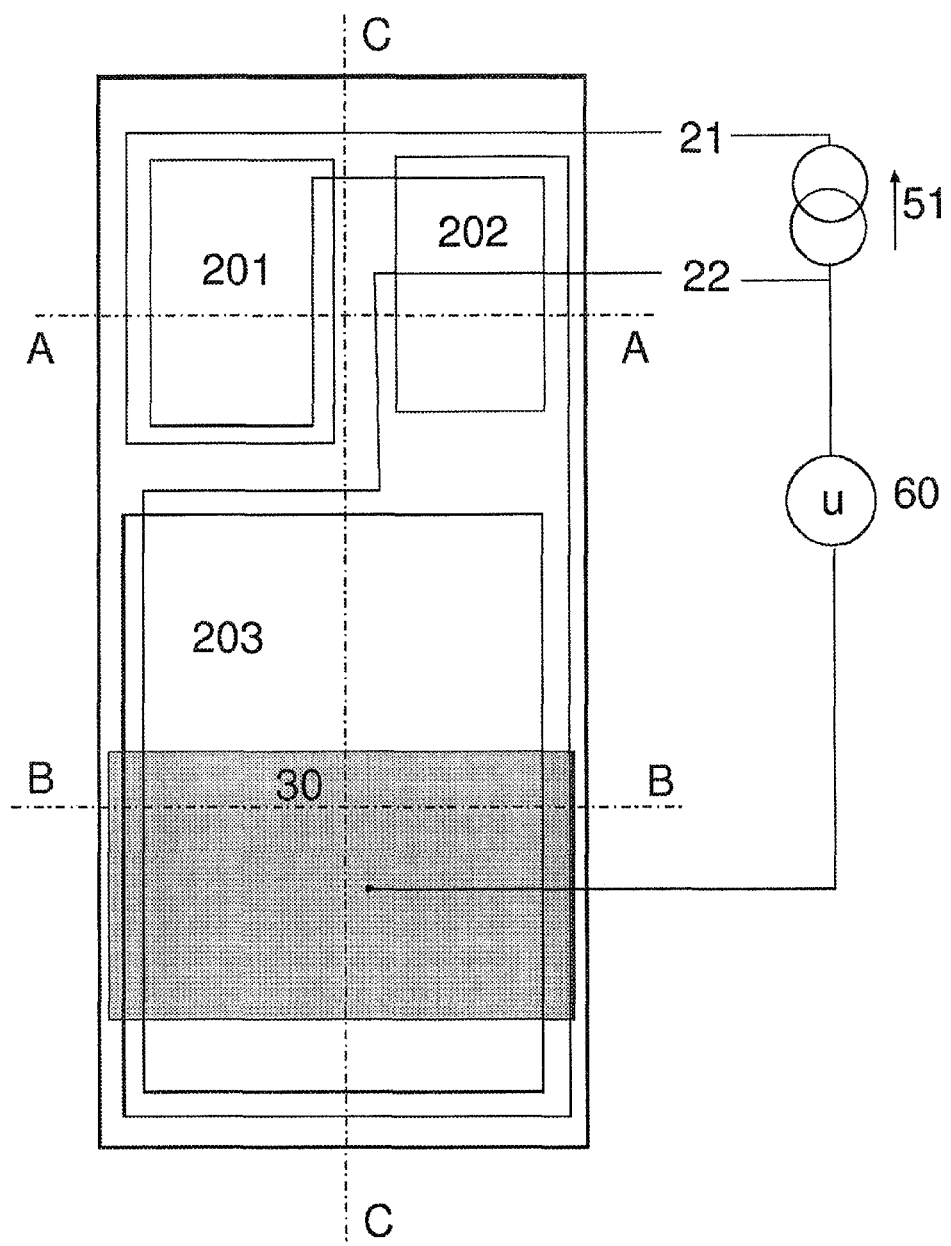
FIG. 5 is a view of a special embodiment of the device for creating an electric field combined with a magnetic field.

FIG. 5 shows a special embodiment of the device for creating an electric field combined with a magnetic field, with the coil system being embodied such that a field distribution can develop adjusted to the physiology of the creature, representing either a human or an animal.

In this embodiment, the freedom for designing the coils that create the magnetic field is shown in an embodiment of the applicator according to FIG. 4. FIG. 5 shows the coil system between the connector 21 and 22 comprising partial coils 201 and 202 as well as 203. Furthermore, an electrode 30 is shown for the electric field.

The arrangement of the coils 201 and 202 is designed such that the current flows in the opposite direction. This way, the magnetic field is concentrated in the center, as discernible from the diagram of the distribution of the field strength in FIG. 8, section A-A. The arrangement of the coil 203 has been selected such that the embodiment of the magnetic field, strong over the lateral coil conductors, is optimally effective below the extremities, as shown in the diagram of the distribution of the field strength in FIG. 8, section B-B. The effect of the electrode is shown in FIG. 7, section C-C, as a diagram of field strengths.

Figure 6:
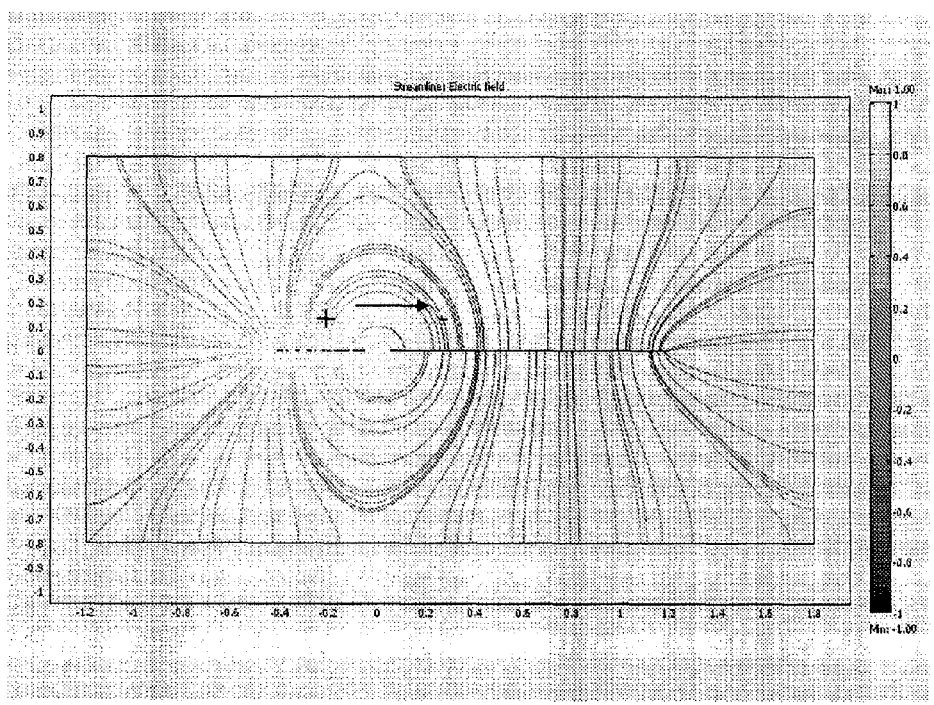
FIG. 6 is a graph showing the distribution of the electric field between the upper and the lower coil in a device according to FIG. 3.

The distribution of the electric field between the upper and the lower coil is discernible from FIG. 6 in an arrangement according to FIG. 3. The flux lines can form, for example, between the positive potential of the coil 20 and a respective negative potential of the coil 30. The symmetric embodiment upward and downward is discernible.

Figure 7:
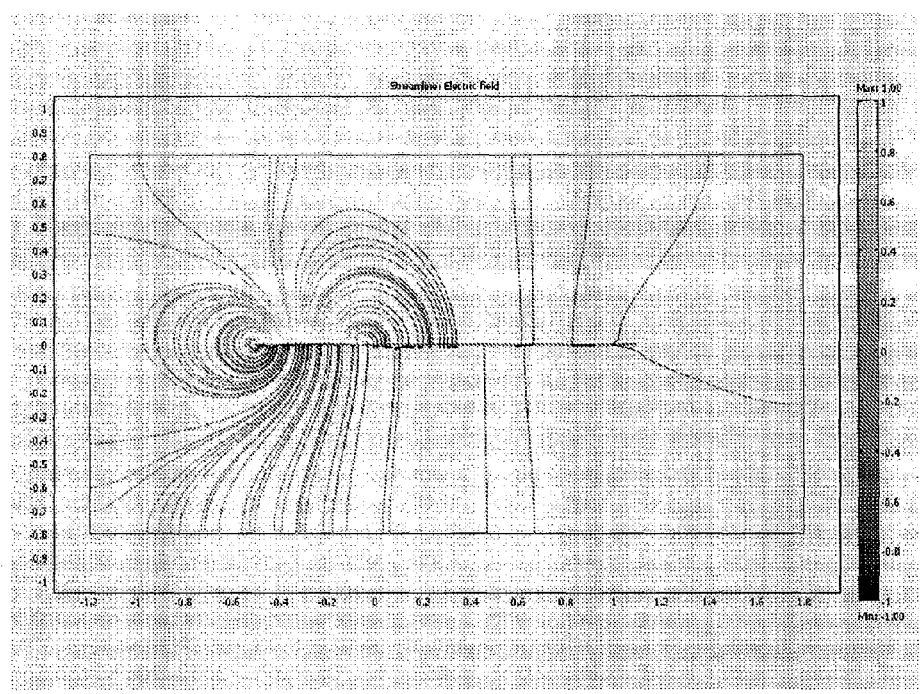
FIG. 7 is a graph showing the distribution of the electric field between an electrode and a coil system in an arrangement according to FIG. 4 or 5.

FIG. 7 shows the flux lines of an electric field, which develops, for example, between a positive electrode and the respective negative coil system. The lines each connect the positive, light side with the negative, dark side of the potential.

Figure 8:
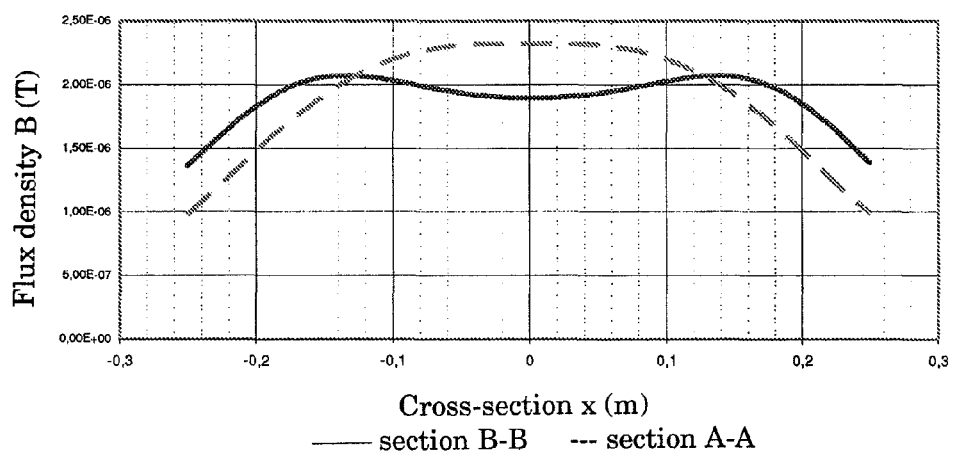
FIG. 8 is a graph showing the progression of the magnetic flux density over a coil arrangement adjusted to the physiological conditions.

FIG. 8 shows the progression of the magnetic flux density over the coil arrangement adjusted to the given physiological conditions, with the diagram of the continuous line representing the progression in the area of section B-B (see FIG. 5) and the dot-dash line the progression in the area of the section A-A (see FIG. 5). The concentration of the field strength on the central area is discernible in section A-A, which is arranged preferably in the area of the spine, and the distribution of the field strength maximums at two sides such that this arrangement is preferred for the extremities.

Figure 9:
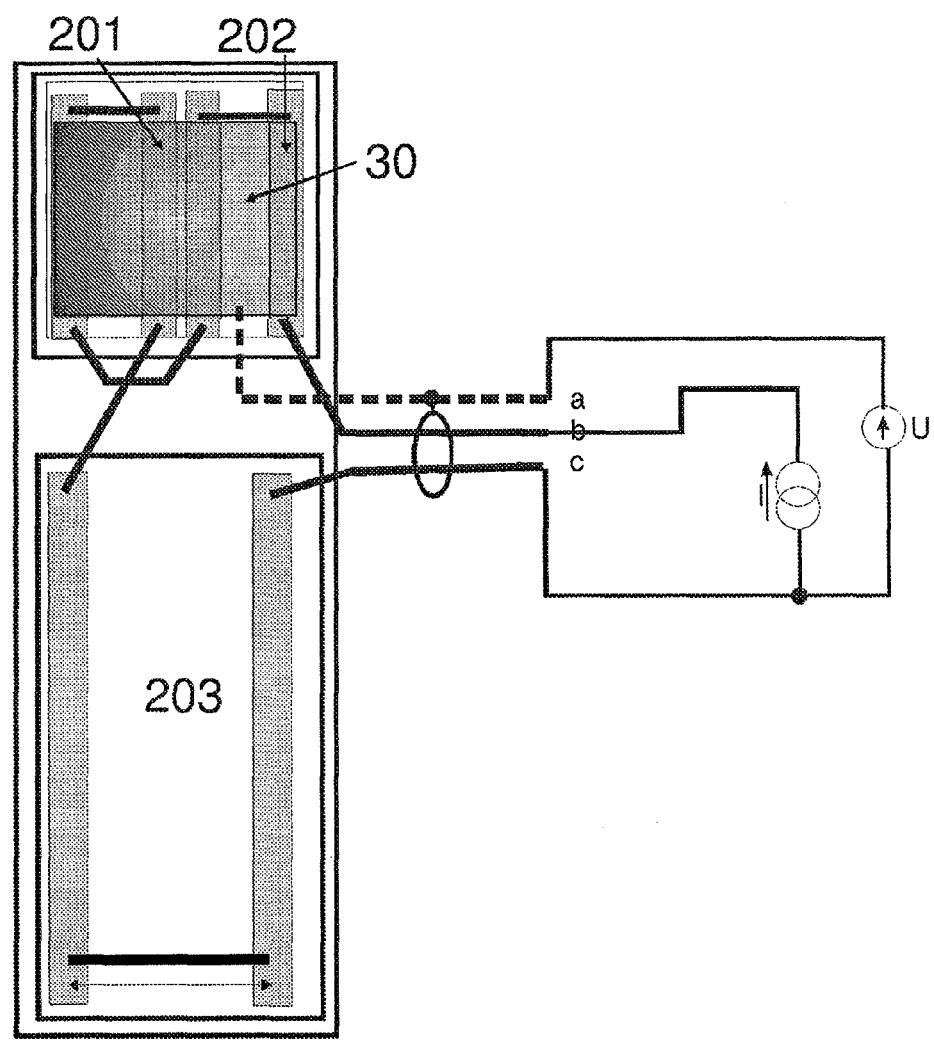
FIG. 9 is a view of an embodiment of the device for creating an electric field combined with a magnetic field according to the embodiment of FIG. 5.

FIG. 9 shows an embodiment of the device to create an electric field combined with a magnetic field similar to the embodiment according to FIG. 5, with the coils 201, 202, and 203 only comprise a flat, level current loop. These level, parallel current paths can for example be integrated in a mat applicator, by conductive tape being implemented by way of electrically conducting yarn in form of warp and/or weft threads. Here, the conductive tapes are connected at one part such that a coil system develops adjusted to the given physiological conditions, with each of the coils of the system comprising only a single electric loop.

The current for creating the magnetic field is introduced through the power source I into the connector b. After the current has flown through the coils 202 and 201, it is guided in coil 203 into the lower area and then via the connector c back to the power source. Using the voltage source U, an electric field is created between the electrode 30 and the coil system 201, 202, 203 by connecting the voltage via the connector a to the electrode 30 and via the connector c to the coil system.

In order to achieve a simple embodiment of the connection cable and to ensure an interfering influence of the environment being as little as possible, the connection cable is embodied with the conductors a, b, and c such that the electrically conductive wires a and b are twisted and the conductor c is pulled over the wires a and b as a shield. The arrangement of the coils occurs preferably such that the coils 201 and 202 become effective in the area of the spine of a human being or, if applicable, a vertebrate, and the coil 203 reaches its effectiveness in the area of the extremities, particularly the legs. In order to provide an optimal arrangement, here the distance between the upper and the lower coils can be designed in a variable fashion.

The distance at the longitudinal power path in the coil 203 is to be adjusted to the legs such that the maximums discernible in FIG. 8 section B-B can optimally stimulate the magnetic flux density to the nerve tract as well as the peripheral blood vessels in the extremities.

Figure 10:
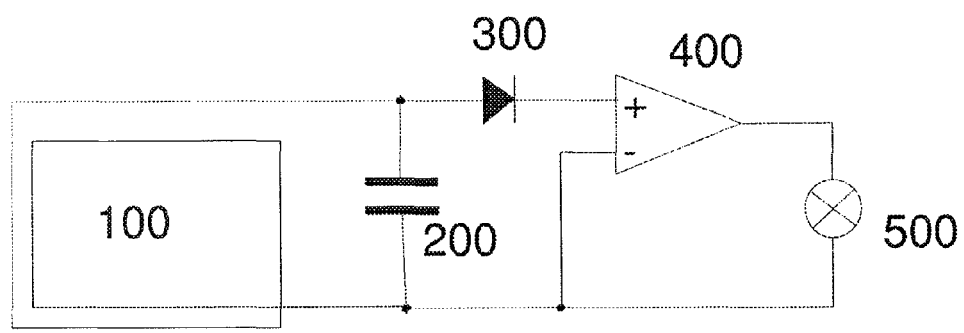
FIG. 10 is a diagram of a simple device for checking the functionality of the device for stimulating probands via special electric and magnetic fields as well as optimized field applicators.

FIG. 10 shows a simple device to check the functionality of the device for crating a combined electric and magnetic field with frequencies selected for the intended effect.

This device includes a coil 100, together with the condenser 200 forming a resonance circle, adjusted to the characteristic frequency of the signal mixture of the $i_{IIS}$—signal, e.g., 1000 Hz, and thus not registering 50 Hz—interference signals and other ones. The detector 300, in the simplest case a diode, creates a control signal from the alternating voltage induced by the stimulus signal in an oscillating circuit, which is enhanced by the amplifier 400, if applicable. The control signal is indicated by an indicator 500, which in the simplest case may be a light emitting diode, however, it may also have several display states.

Following the same algorithm according to FIG. 10, a generalized device is realized according to the invention such that in addition to the device for checking the functionality of the device for creating a combined electric and magnetic field with the frequencies used for the desired effect additionally and simultaneously, via a separate system of coil/resonance circuit, the detection of 50 and/or 60 Hz interference signals is possible.

Figure 11:
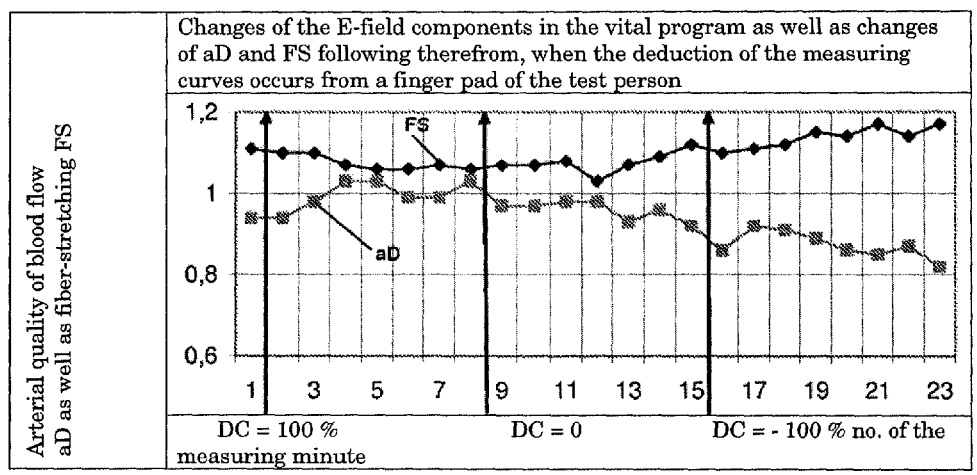
FIG. 11 is a graph of the characteristic progression of peripheral blood circulation parameters, deducted from the non-invasive NIRP-method of the measuring site finger pad in a 40-year old normal probands, with changes of the E-field components of a stimulation program, in the exemplary embodiment "Vitality"

FIG. 11 shows that a reversal of the polarity of measures performed generally leads to a reduction of the quality of arterial blood flow as well as a worsening of the elasticity of the blood vessels (=increase of fiber stretching) in this application program. This exemplary embodiment confirms the dependency of the peripheral circulatory parameters in an E-field between the area near the head and the periphery.

Figure 12:
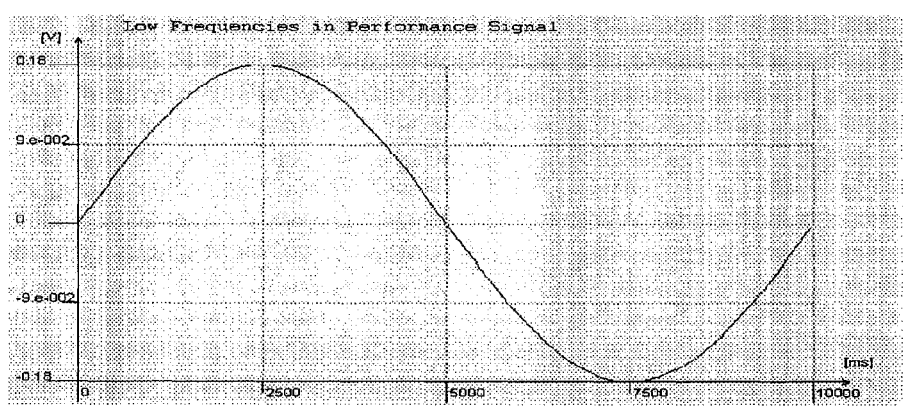
FIG. 12 is a graph of an oscillation period of low-frequency sympathetic (a) as well as parasympathetic (b) control frequency as the basic oscillation of a corresponding stimulation program.
Figure 12:
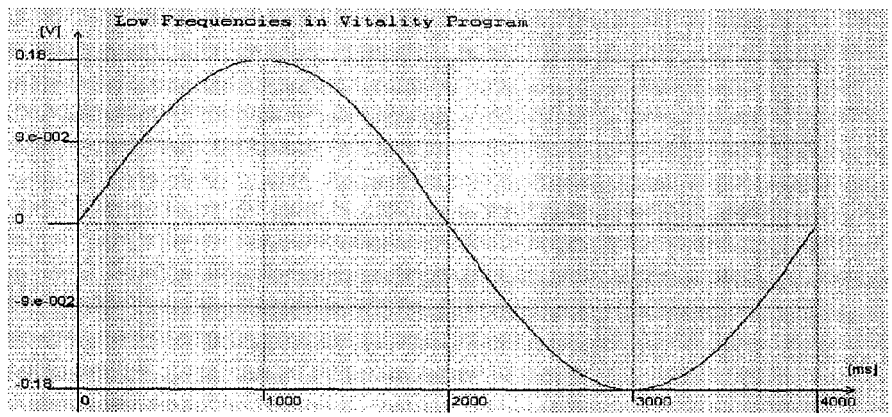

In FIG. 12 an oscillation period of the low-frequency sympathetic (a) as well as the parasympathetic (b) control frequency is shown as the basic oscillation of an appropriate stimulation program. The sympathetic (0.1 Hz=10 s oscillation period) and/or parasympathetic (0.25 Hz=4 s oscillation period) basic oscillations are interfered by appropriately higher-frequency oscillations, as discernible from FIGS. 13 as well as 15 and 17.

Figure 13:
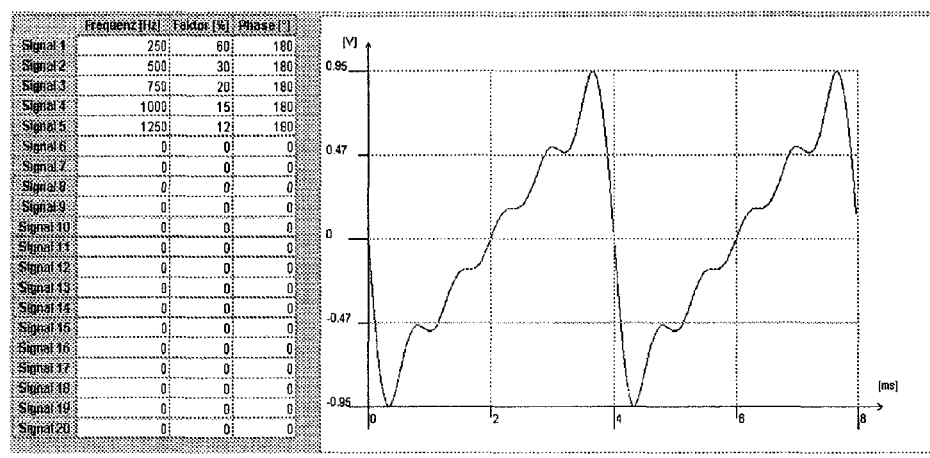
FIG. 13 is a graph of the periodic progression of a defined higher-frequency III-function $i_{IIS}(t)$ [iis . . . ion injection signal] with the periods from 4 ms=250 Hz and the frequencies 250, 500, 750, 1000, and 1250 Hz, if the respective amplitudes of these oscillations have the relative portions 1, ½, ⅓, ¼, ⅕, ⅙.

The IIS-function $i_{IIS}(t)$ according to FIG. 13 interferes with the stimulation programs, especially the control frequencies 0.1 and 0.25 Hz as well as respective EEG-frequencies and the frequency 100 Hz, in order to dissolve primarily any (pathological) erythrocytic aggregation occurring and to achieve improved blood flow characteristics. These results can be deduced from measurements of capillary flow and microscopic blood dark area imaging.

Figure 14:
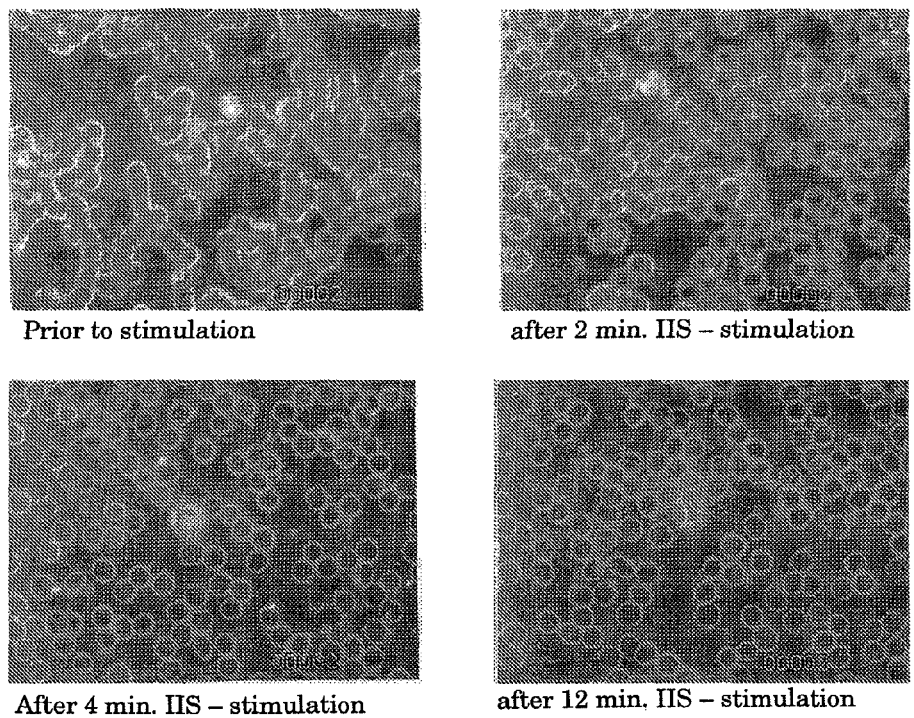
FIG. 14 is photographs of a result, to be a generalized exemplary embodiment, of blood dark area images taken from a 55-year old diabetes patient prior, after 2, 4, and 12 minutes of stimulation with the IIS-function $i_{IIS}(t)$ according to FIG. 13.

It is discernible from FIG. 14 how the erythrocytes separate under a stimulation with the IIS-function $i_{IIS}(t)$ according to FIG. 13, with obviously pathologic erythrocytic aggregation had existed prior to the stimulation. It has been learned according to the invention, in a stimulation first only to allow such an ISS signal to act for approximately 4 minutes, and subsequently to activate the stimulation application program (see FIGS. 15 through 17).

Figure 15:
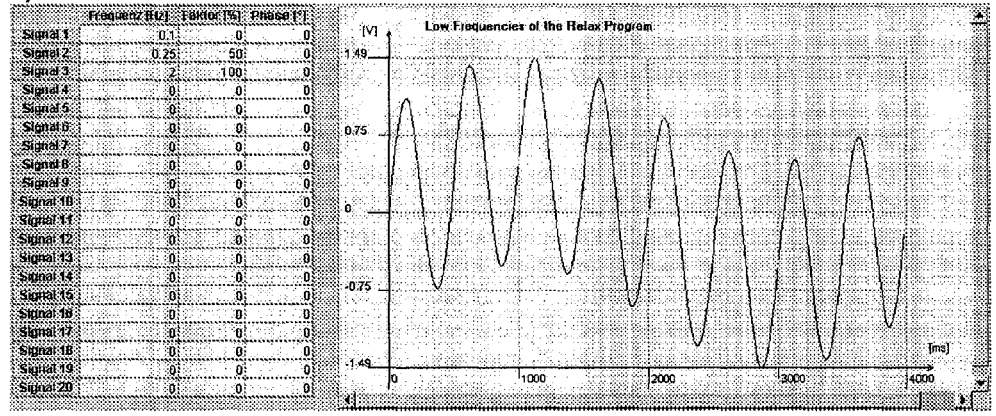
FIG. 15 is graphs of the characteristic oscillation frequencies, interfered with the parasympathetic control frequencies of 0.25 Hz, for a stimulation program "Relax" as the exemplary embodiment:
a) a basic oscillation 0.25 Hz with a relative amplitude of 50% and a relax-reference frequency (EEG-delta frequency) of 2 Hz at 100% amplitude ratio,
b) an EEG-alpha frequency of 100 Hz with 50% and 100 Hz with 40% of the reference signal (reference frequency) of 2 Hz,
c) an overall signal from adding a) and b) as well as $i_{IIS}(t)$ [see FIG. 13] for the stimulation period of 4 s, equivalent to the period of the basic oscillation of 0.25 Hz=4 s.
Figure 15:
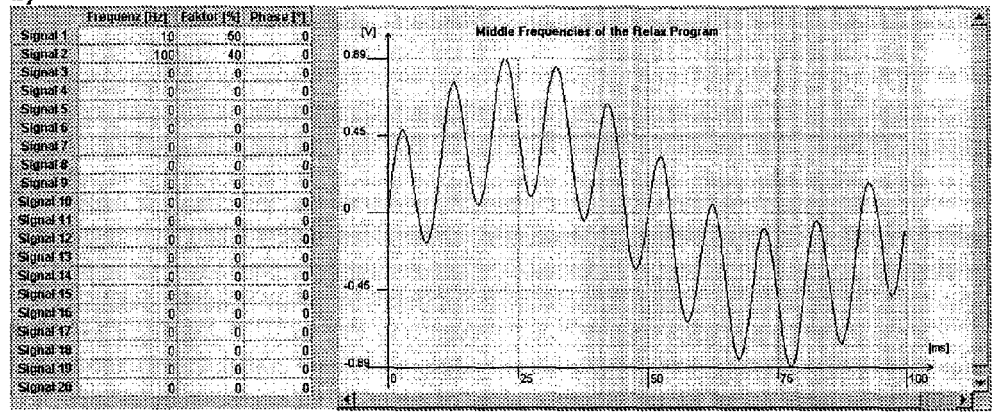
Figure 15:
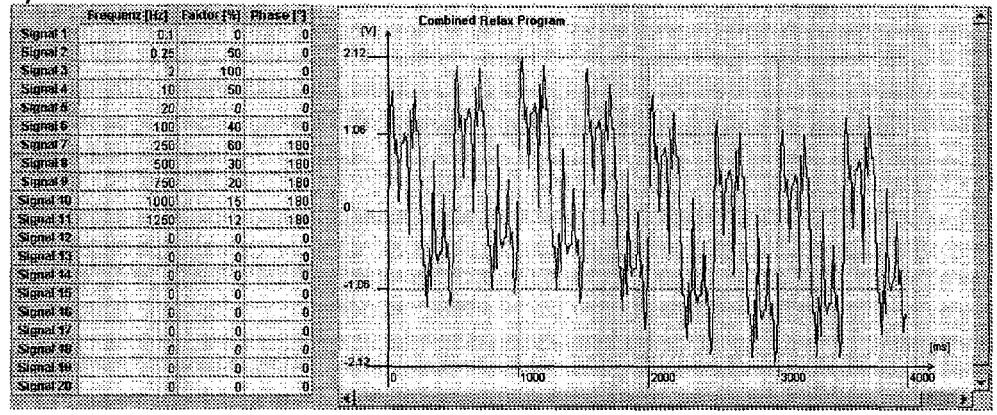
Figure 16:
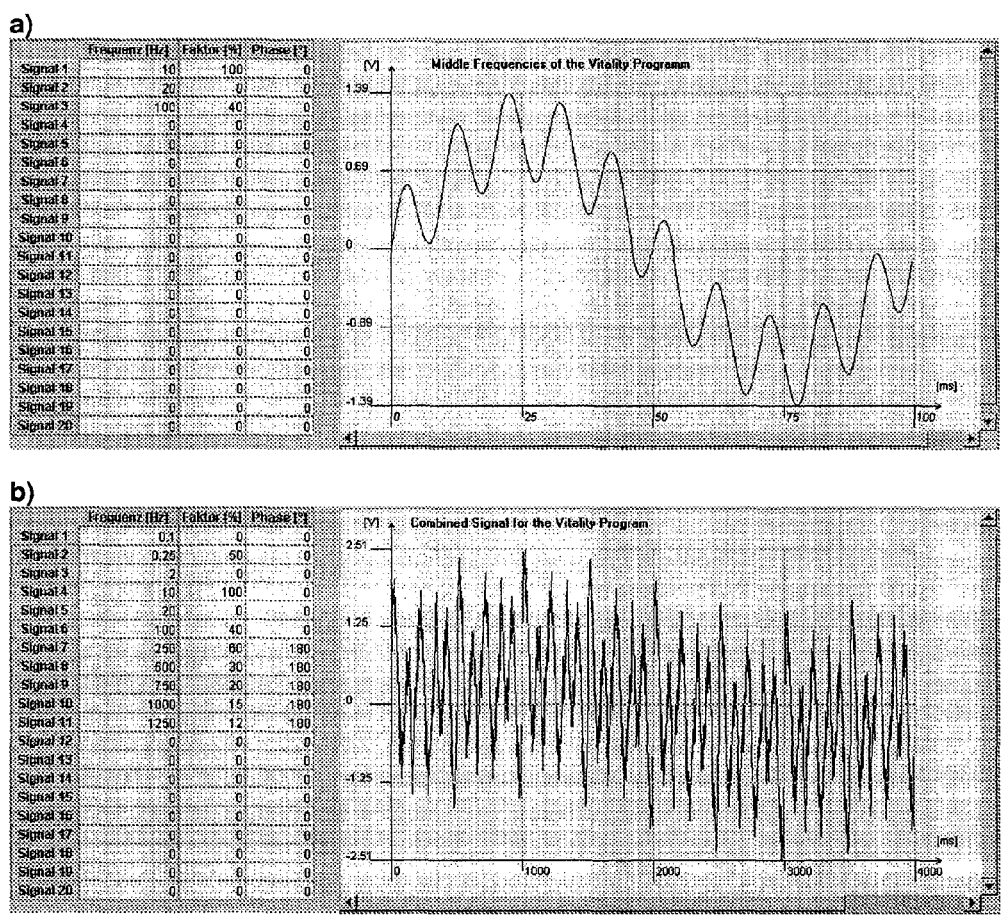
FIG. 16 is graphs of the characteristic oscillation frequencies interfered by the parasympathetic control frequency of 0.25 Hz for a stimulation program "Vitality" representing the exemplary embodiment:
a) a vitality reference frequency of 10 Hz (EEG-alpha frequency) at 100% amplitude ratio as well as 100 Hz at 40% amplitude ratio,
b) an overall signal from adding a) as well as 0.25 Hz (50% amplitude ratio, see FIG. 12) and $i_{IIS}(t)$ [see FIG. 13] for the stimulation period of 4 s, which is equivalent to the period of the basic oscillation of 0.25 Hz=4 s.
Figure 17:
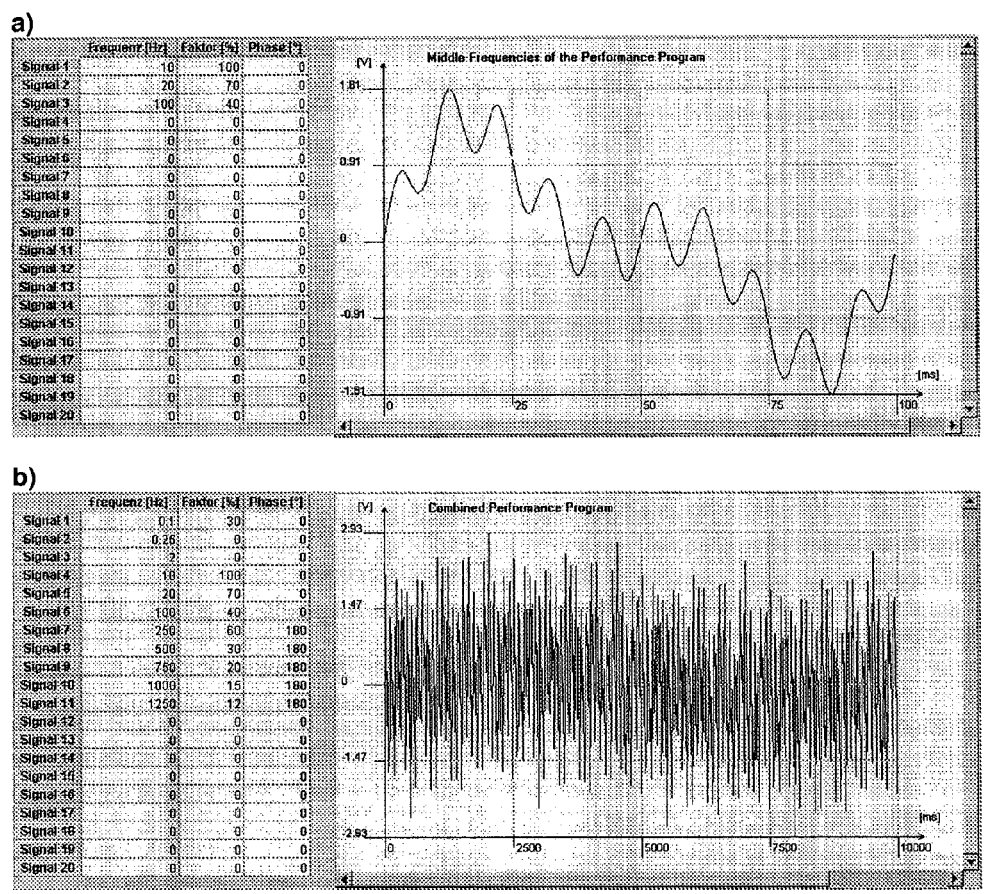
FIG. 17 is graphs of the characteristic oscillation frequencies, which are interfered with the sympathetic control frequency 0.1 Hz, for a stimulation program "Performance" representing an exemplary embodiment:
a) a performance reference frequency of 10 Hz (EEG alpha-frequency) at 100% amplitude ratio and 20 Hz at 70% amplitude ratio as well as 100 Hz at 40% amplitude ratio,
b) an overall signal from adding a) as well as 0.1 Hz (50% amplitude ratio, see FIG. 12) and $i_{IIS}(t)$ [see FIG. 13] for the stimulation period of 10 s, which is equivalent to the period of the basic oscillation 0.1 Hz-10 s.

While in FIG. 15 for the stimulation program "Relax" the frequency of 2 Hz shows a typical EEG—delta frequency and in such delta frequencies highly significant changes of insomnia appear, there are also highly significant results, among other things, for immuno-biologic reactions, edema inhibition, sensitivity to weather, improvement of concentration, general increase in performance with 10 Hz-fields (also see the stimulation programs "Vitality" and "Performance" according to FIGS. 16 and 17).

The invention claimed is:

1. A device for stimulation via electric and magnetic fields, comprising:
    means for generating a stimulation signal for external physical stimulation of a vegetative / autonomic nervous system as a control component of a cardiovascular system with parts of a sympathetic and parasympathetic nervous system within a corresponding physiologic frequency range of 0.05 to 0.15 or 0.16 to 0.30 Hz,
    means for a gradual wobbling or sweeping in the corresponding frequency range with a step size of 0.1 Hz or for a continuous running through of the frequency range,
    means for adding characteristic sinusoidal oscillations and adapted for creating a positive or negative E-field between a head and a peripheral area of a proband area of a central nervous system for forming a modular overall stimulation signal with the sympathetic or parasympathetic control frequency as a basic oscillation provided by the means for external physical stimulation and wherein the means for adding adds EEG-frequencies and higher frequency sinusoidal oscillations at a Fourier-sequence of a fundamental oscillation of 250 Hz and harmonic oscillations of 500, 750, 1000, 1250, 1500 Hz to the stimulation signal for the external physical stimulation of the vegetative / autonomic nervous system.

2. A device according to claim 1, further comprising field applicators in the form of mat applicators for receiving the stimulation signal and adapted to create a magnetic field with a magnetic flux, wherein the field applicators are used for coupling in energy from the magnetic field, which ensure that a concentration of the magnetic flux created by the mat applicator that is adapted to be located in an upper body area of the proband adjusts to a center of the body and based on physiological conditions, the mat applicator that is adapted to be located at a lower half of the body such that a distribution of the magnetic field energy is adapted to occur to both legs, with centers thereof being a certain distance in reference to each other, and thus two maximums for field strengths result.

3. A device according to claim 2, wherein the field applicators comprise a combined coil arrangement adapted to create the magnetic field and adapted to create an electric field in order to combine advantages of the external physical stimulation via an electric potential difference created between the field applicators with an input of effects of the magnetic fields.

4. A device according to claim 3, wherein the applicators comprise various individual coils or coils in combination with electrically conductive grids or surfaces allowing both an introduction of electric currents as well as electric voltages.

5. A device according to claim 1, wherein the means for external physical stimulation further comprise a coil-condenser oscillation circuit that provides the stimulation signal, and a detector that is adapted to check an effectiveness of the stimulation device, wherein display statuses based on an effectiveness of the stimulation device are adapted to be provided via the detector.

* * * * *